United States Patent
Wang et al.

(10) Patent No.: US 12,383,573 B2
(45) Date of Patent: Aug. 12, 2025

(54) USE OF LUTEOLIN-7-O-GLUCOSIDE OR LUTEOLIN-7-O-GLUCURONIDE IN PREPARATION OF MEDICINE FOR EYE INJURIES

(71) Applicant: BEIJING CHENGYI INVESTMENT CO., LTD., Beijing (CN)

(72) Inventors: Hao Wang, Beijing (CN); Xuexiang Cheng, Beijing (CN)

(73) Assignee: BEIJING CHENGYI INVESTMENT CO., LTD., Beijing (CN)

( * ) Notice: Subject to any disclaimer, the term of this patent is extended or adjusted under 35 U.S.C. 154(b) by 838 days.

(21) Appl. No.: 17/598,913

(22) PCT Filed: Aug. 20, 2019

(86) PCT No.: PCT/CN2019/101567
§ 371 (c)(1),
(2) Date: Sep. 28, 2021

(87) PCT Pub. No.: WO2020/199460
PCT Pub. Date: Oct. 8, 2020

(65) Prior Publication Data
US 2022/0160742 A1 May 26, 2022

(30) Foreign Application Priority Data
Apr. 4, 2019 (CN) .......................... 201910271900.2

(51) Int. Cl.
*A61K 31/7048* (2006.01)
*A23L 29/00* (2016.01)
*A61P 27/02* (2006.01)

(52) U.S. Cl.
CPC ........ *A61K 31/7048* (2013.01); *A23L 29/035* (2016.08); *A61P 27/02* (2018.01)

(58) Field of Classification Search
None
See application file for complete search history.

(56) References Cited

U.S. PATENT DOCUMENTS

| | | |
|---|---|---|
| 2007/0184133 A1 | 8/2007 | Tripp |
| 2010/0278914 A1 | 11/2010 | Kim et al. |

FOREIGN PATENT DOCUMENTS

| | | |
|---|---|---|
| CN | 102316884 A | 1/2012 |
| CN | 102512433 A | 6/2012 |
| CN | 103933058 A | 7/2014 |
| CN | 106074585 A | 11/2016 |
| CN | 106880626 A | 6/2017 |
| CN | 108159143 A | 6/2018 |
| CN | 108938687 A | 12/2018 |
| CN | 109876003 A | 6/2019 |
| CN | 110025625 A | 7/2019 |
| WO | 2009025532 A2 | 2/2009 |

OTHER PUBLICATIONS

Quinn, Int J. Mol. Sci. 2014, 15, 1441-1465. (Year: 2014).*
Tian, Heliyon, vol. 5, Issue 8, Aug. 2019. (Year: 2019).*
Heiting, Blue Light and Displays, internet article, https://eyesafe.com/chapter-2/#:~:text=This%20scattering%20is%20why%20the,energy%20%E2%80%94%20of%20all%20visible%20light, downloaded from the internet Aug. 1, 2024. (Year: 2024).*
Ma, CN 102512433A, 2012, machine translation. (Year: 2012).*
Wang, CN109876003A, Jun. 2019, machine translation. (Year: 2019).*
Masaki tanato, On the adverse effects of blue light, retinal disorders caused by blue light, 31(2):175-182; the year of 2014, Nihonbashi midori eye clinic, effects of retina,https://www.midori-eye-clinic.jp/bluelight.
T.H. Margrain et al., Do blue light filters confer protection against age-related macular degeneration?Progress in Retinal and Eye Research, 2004, p. 523-531, doi:10.1016/j.preteyeres.2004.05.001.
Sung Wook Park et al., Luteolin extracted from Platycodon grandiflorum protects retinal pigment epithelial cells from oxidative stress-induced caspase-3 dependent apoptosis, Biomedicine & Preventive Nutrition, 2011, p. 77-80, doi:10.1016/j.bionut.2011.12.009.
Kayoko Shimoi et al., Intestinal absorption of luteolin and luteolin 7-o-β-glucoside in rats and humans, FEBS Letters, 1998, p. 20-224, DOI: 10.1016/s0014-5793(98)01304-0.
Soumyajit Majumdar et al: "Potential of the bioflavonoids in the prevention/treatment of ocular disorders", Journal of Pharmacy and Pharmacology, Jan. 1, 2010 (Jan. 1, 2010), pp. 951-965.
Chang Chi-Huang et al: "Photoprotective effects of cranberry juice and its various fractions against blue light-induced impairment in human retinal pigment epithelial cells", Pharmaceutical Biology, vol. 55, No. 1,Dec. 9, 2016 (Dec. 9, 2016), pp. 571-580.
The Japanese 1st Office Action dated Sep. 13, 2022 for JP2021-560375.
European search Report issued on Nov. 17, 2022 for EP19922400.7.
International Search Report for PCT/CN2019/101567 mailed Dec. 27, 2019, ISA/CN.
Park. Y.H., et al."Effect of hydroxy groups in natural flavones on ocular blood flow of rabbits and retinal function recovery after ischemia insult in rat eyes ," International Journal of Ophtalmology, vol. 4, No. 1, Feb. 25, 2004 (Feb. 25, 2004). pp. 1-6.
Maria Hytti, et al., Fisetin and luteolin protect human retinal pigment epithelial cells from oxidative stress induced cell death and regulate inflam, Scientific Reports, Dec. 1, 2015, p. 2-13.

* cited by examiner

*Primary Examiner* — Layla D Berry
(74) *Attorney, Agent, or Firm* — Yue (Robert) Xu; Apex Attorneys at Law, LLP

(57) ABSTRACT

Provided is the use of luteolin-7-O-glucoside or luteolin-7-O-glucuronide in the preparation of a medicine for eye injuries, wherein same falls within the technical field of medicines. Further provided is the use of luteolin-7-O-glucoside and/or luteolin-7-O-glucuronide in the preparation of a medicine for treating eye injuries caused by blue light. An in vitro drug effect screening model experiment of blue light-induced damage of retinal pigment epithelial cells proves that the luteolin-7-O-glucoside and luteolin-7-O-glucuronide have an efficacy in protecting retinal pigment epithelial cells from damage caused by blue light. Therefore, the luteolin-7-O-glucoside and lutecolin-7-O-glucuronide may also be used in eye-protection health products or foods.

6 Claims, 3 Drawing Sheets

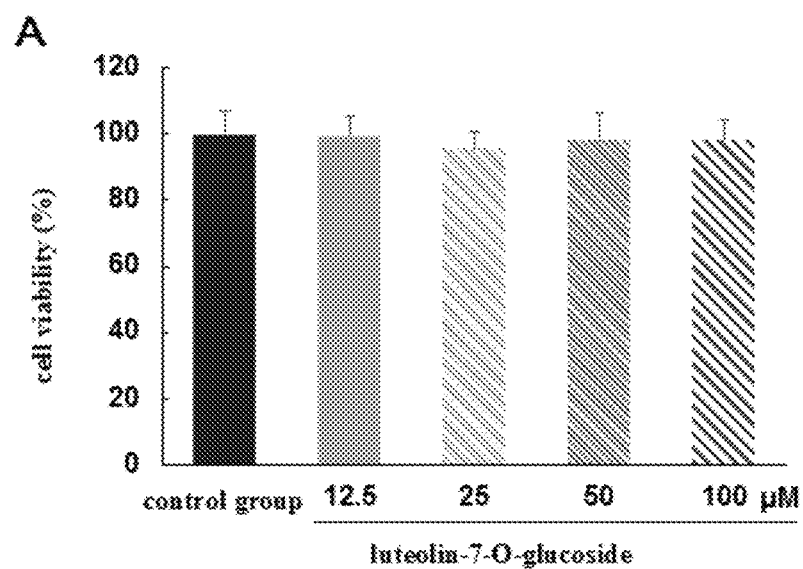
FIG. 1-A
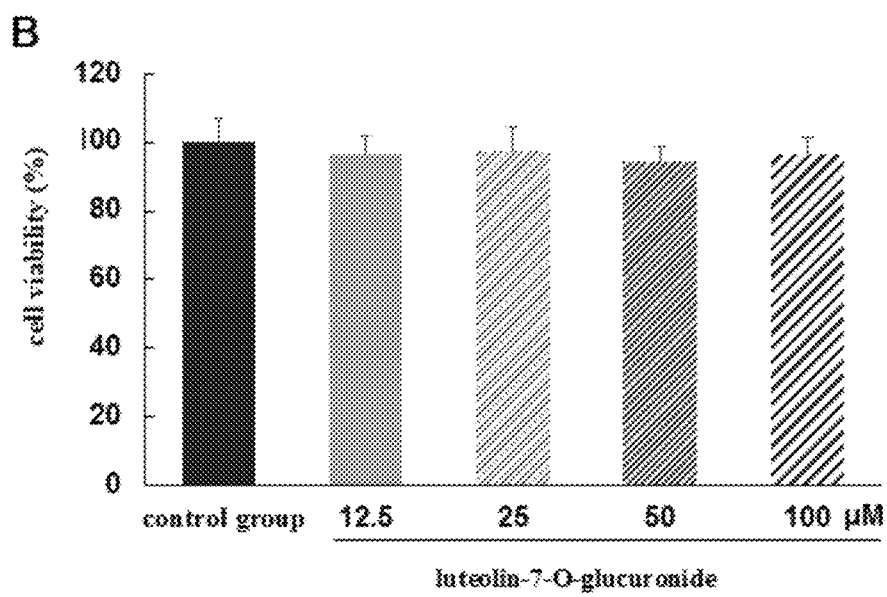
FIG. 1-B

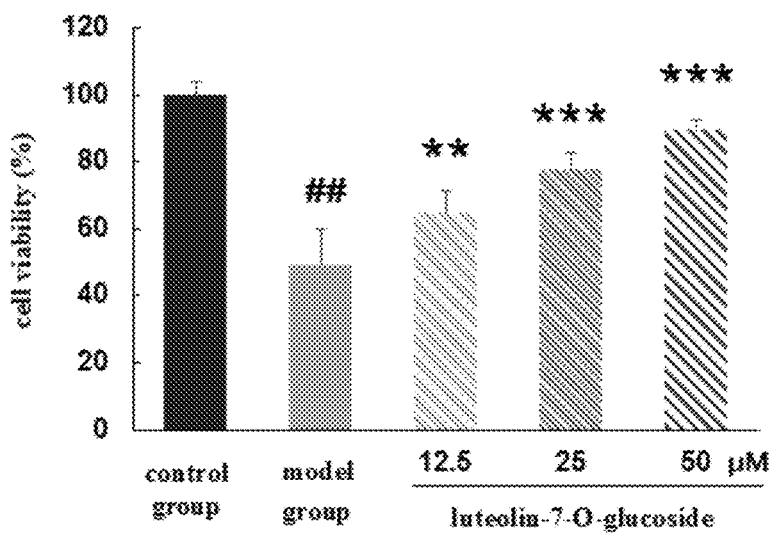
FIG. 2-A
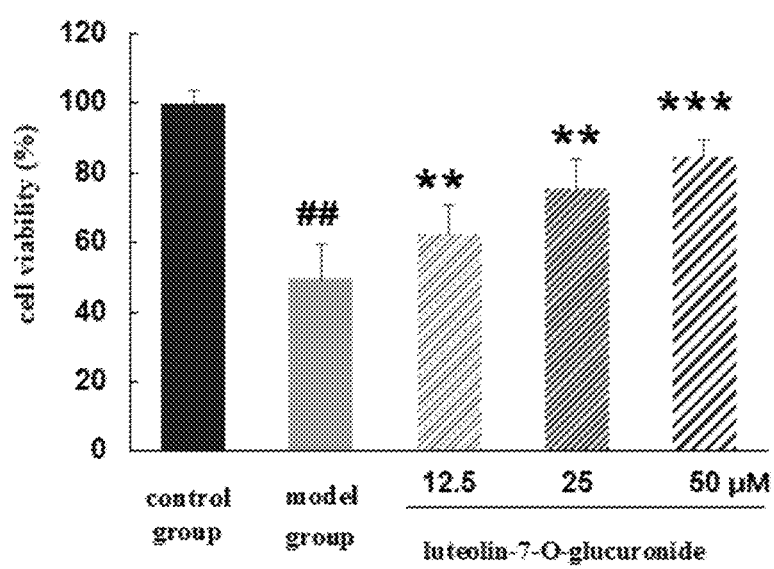
FIG. 2-B

USE OF LUTEOLIN-7-O-GLUCOSIDE OR LUTEOLIN-7-O-GLUCURONIDE IN PREPARATION OF MEDICINE FOR EYE INJURIES

The present application is the national phase of International Application No. PCT/CN2019/101567, titled "USE OF LUTEOLIN-7-O-GLUCOSIDE OR LUTEOLIN-7-O-GLUCURONIDE IN PREPARATION OF MEDICINE FOR EYE INJURIES", which claims the priority to Chinese Patent Application No. 201910271900.2, titled "USE OF LUTEOLIN-7-O-GLUCOSIDE OR LUTEOLIN-7-O-GLUCURONIDE IN PREPARATION OF MEDICINE FOR EYE INJURIES", filed on Apr. 4, 2019 with the Chinese Patent Office, which are incorporated herein by reference in their entireties.

FIELD

The present disclosure relates to the technical field of pharmaceuticals, and specifically relates to the use of luteolin-7-O-glucoside or luteolin-7-O-glucuronide in preparation of eye injury medicines.

BACKGROUND

Eyes are the organs of the human body that receive external light stimulation and produce vision. The cornea and lens of the eye are transparent structures, and the light-gathering effect of which is used by light to focus on the retina, stimulating the photoreceptor cells to produce vision. Harmful light can also enter the eyes through this route, which can easily cause dry eyes, eye fatigue, eye injury, dark circles, eye wrinkles and the like.

Modern people live in an environment surrounded by various screens, including mobile phones, tablets, televisions, and various monitors. The background light source of these screens is excited by a powerful electron current. The screen light source contains abnormal high-energy blue light, and this kind of short-wavelength light can penetrate the lens of the human eyes to reach the retina. The photoreceptor cells of the retina have cell membranes with a special structure, which is rich in fatty acids. Under excessive blue light exposure, they are particularly prone to peroxidation and accumulation of free radicals, which promote the apoptosis of retinal pigment epithelium (RPE), causing damage to eyesight.

At present, there are many drugs for retinal injuries. For example, Patent Publication No. CN 108938687A discloses the application of *Tribulus terrestris* in the manufacture of a medicament for the prevention and treatment of retinal injury diseases, and reveals that the extract of *Tribulus terrestris* has a protective effect on hydrogen peroxide ($H_2O_2$)-induced oxidative stress damage to human retinal pigment epithelial cells. Patent Publication No. CN 106880626A discloses the protective effect of kaempferol on retinal pigment epithelial cells under oxidative stress. Patent Publication No. CN 106074585A discloses the intervention effect of the combination of ginsenoside Rb 1 and Rd on retinal light injury mouse model, and the results show that the pharmaceutical combination can antagonize retinal pigment epithelial cell oxidative stress, effectively inhibit retinal injury-related immune inflammation, and significantly improve retinal degenerative diseases.

Luteolin-7-O-glucoside and luteolin-7-O-glucuronide are both known compounds in the prior art, extracted from *Elsholtzia bodinieri* vaniot and Sowthistle-leaf ixeris. Luteolin-7-O-glucuronide has the effects of treating cardiovascular diseases, improving microcirculation, and lowering blood lipids. Luteolin-7-O-glucoside has the effects of anti-hepatitis B virus and treatment of dementia. The raw materials of luteolin-7-O-glucoside and luteolin-7-O-glucuronide are readily available, and it is of great significance to develop new applications of the two compounds.

SUMMARY

In view of this, the purpose of the present disclosure is to provide a new use of luteolin-7-O-glucoside or luteolin-7-O-glucuronide, specifically use of compound luteolin-7-O-glucoside or luteolin-7-O-glucuronide in the manufacture of a medicament for preventing or treating an eye injury.

The present disclosure provides use of luteolin-7-O-glucoside as shown in formula I or luteolin-7-O-glucuronide as shown in formula II in the manufacture of a medicament for preventing or treating an eye injury, of an eye care health product and of a food;

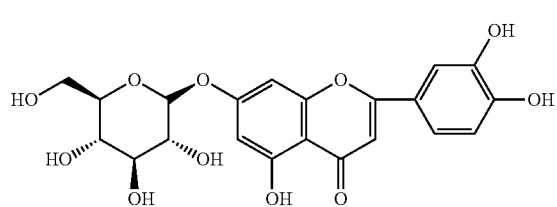

Formula I

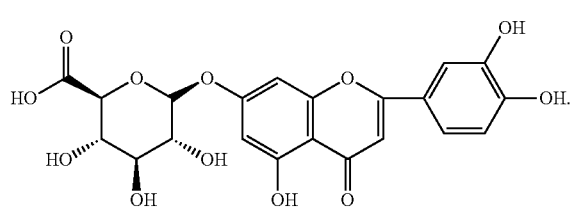

Formula II

Preferably, the eye injury is human retinal injury.
Preferably, the human retinal injury is human retinal pigment epithelial cell injury.
Preferably, the eye injury is an eye injury caused by blue light.
Preferably, the blue light is short-wave blue light; and the wavelength of the short-wave blue light is 400~500 nm.
Preferably, the blue light includes the blue light emitted by a mobile phone, a tablet, a television, and a computer monitor.
Preferably, the medicament includes an oral preparation and an external ophthalmic preparation;
The oral preparation includes tablet, capsule, granule, pill, ointment and oral solution;
The external ophthalmic preparation includes eye drop, ophthalmic gel and ophthalmic ointment.
Preferably, in the oral preparation, the mass percentage of the luteolin-7-O-glucoside or luteolin-7-O-glucuronide is 5%~50%;
In the external ophthalmic preparation, the mass percentage of the luteolin-7-O-glucoside or luteolin-7-O-glucuronide is 0.1%~20%.
The present disclosure provides use of luteolin-7-O-glucoside as shown in formula I or luteolin-7-O-glucuronide as shown in formula II in an eye healthcare product or a food

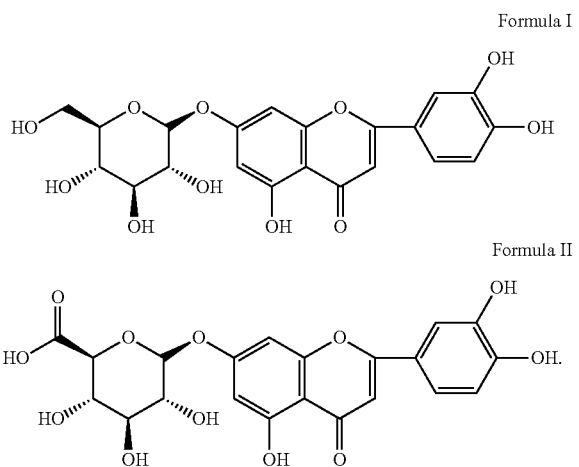

Formula I

Formula II

Preferably, in the eye health care product or food, the mass percentage of the luteolin-7-O-glucoside or luteolin-7-O-glucuronide is 0.1%~20%.

The present disclosure provides use of luteolin-7-O-glucoside as shown in formula I or luteolin-7-O-glucuronide as shown in formula II in the manufacture of a medicament for preventing or treating an eye injury. Cytotoxicity tests show that luteolin-7-O-glucoside and luteolin-7-O-glucuronide have no cytotoxic activity on human retinal pigment epithelial cells ARPE-19, indicating that they have good drug safety. Pharmacodynamic activity tests show that luteolin-7-O-glucoside and luteolin-7-O-glucuronide have the pharmacodynamic effects of preventing and improving blue light-induced damage to ARPE-19 cells. One of the pharmacodynamic mechanisms of luteolin-7-O-glucoside to prevent and improve blue light-induced damage to human retinal pigment epithelial cells ARPE-19 is to reduce the level of reactive oxygen species and apoptosis of cells, thereby ameliorating the damage to human retinal pigment epithelial cells caused by blue light, and improving impaired vision.

BRIEF DESCRIPTION OF DRAWINGS

FIG. 1-A shows the results of the cytotoxicity test of luteolin-7-O-glucoside on human retinal pigment epithelial cells ARPE-19 ($\bar{x}\pm s$, n=3); FIG. 1-B shows the results of the cytotoxicity test of luteolin-7-O-glucuronide on human retinal pigment epithelial cells ARPE-19 ($\bar{x}\pm s$, n=3);

FIG. 2-A shows the results of the pharmacodynamics test of luteolin-7-O-glucoside on blue light-induced damage to human retinal pigment epithelial cells ARPE-19 ($\bar{x}\pm s$, n=3); FIG. 2-B shows the results of the pharmacodynamics test of luteolin-7-O-glucuronide on blue light-induced damage to human retinal pigment epithelial cells ARPE-19 ($\bar{x}\pm s$, n=3); ##P<0.01 vs Control group, P<0.01, *P<0.001 vs Model group;

FIG. 3-A shows the comparison of changes in ROS content in cells of different treatment groups detected by DHE staining; FIG. 3-B shows the comparison of changes in fluorescence intensity in cells of different treatment groups after blue light irradiation detected by DHE staining.

DETAILED DESCRIPTION

Figure 3:
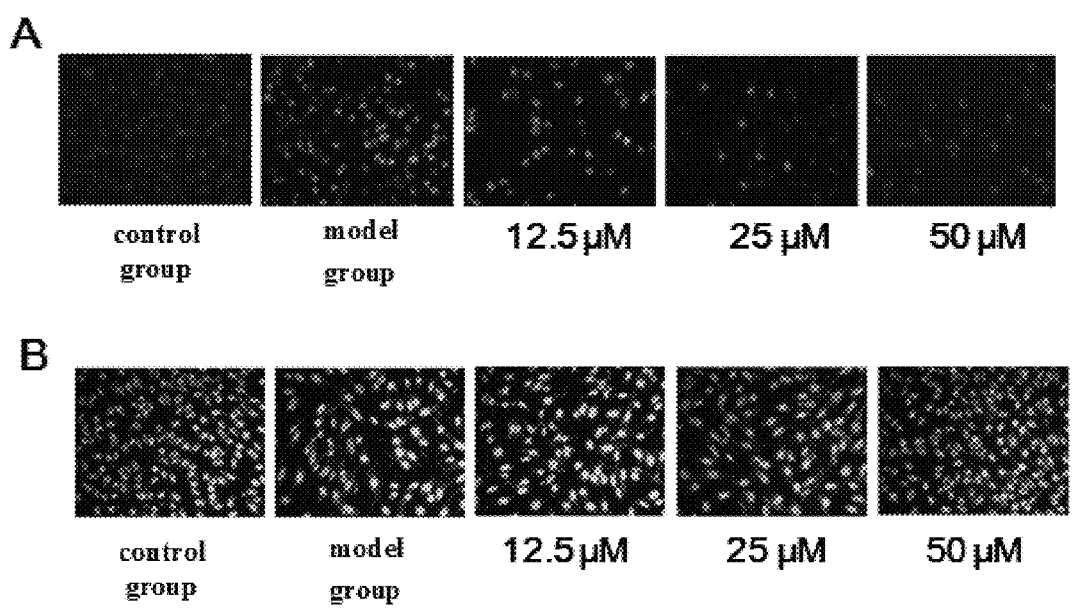
FIG. 3 shows the results of the pharmacodynamic mechanism of luteolin-7-O-glucoside on blue light-induced damage to human retinal pigment epithelial cells ARPE-19.

The present disclosure provides use of luteolin-7-O-glucoside as shown in formula I and/or luteolin-7-O-glucuronide as shown in formula II in the manufacture of a medicament for preventing or treating an eye injury, of an eye care health product and of a food

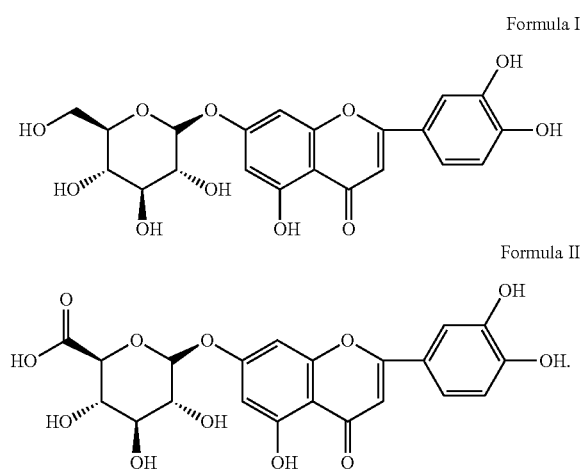

Formula I

Formula II

In the present disclosure, there is no special restrictions on luteolin-7-O-glucoside as shown in formula I or luteolin-7-O-glucuronide as shown in formula II, as long as the two compounds known in the art are used. In the examples of the present disclosure, the luteolin-7-O-glucoside and luteolin-7-O-glucuronide are both purchased from the National Institute for the Control of Pharmaceutical and Biological Products.

In the present disclosure, the eye injury is preferably a human retinal injury. The human retinal injury is preferably an injury caused by a human retinal pigment epithelial cell injury. The eye injury is preferably caused by blue light. The blue light is preferably short-wave blue light; and the wavelength of the short-wave blue light is preferably 400~500 nm. The blue light preferably includes blue light emitted by a mobile phone, a tablet, a television, and a computer monitor. The short-wave blue light can increase the amount of toxins in the macular area of eyes, and seriously threaten people's eye fundus health. Besides, blue light induces eye diseases that might result in blindness.

In the present disclosure, the medicament preferably includes an oral preparation and external ophthalmic preparation. The oral preparation preferably includes tablet, capsule, granule, pill, ointment and oral solution. In the oral preparation, the mass percentage of the luteolin-7-O-glucoside or luteolin-7-O-glucuronide is preferably 5~50%, more preferably 10~40%, most preferably 15%. The external ophthalmic preparation preferably includes eye drop, ophthalmic gel and ophthalmic ointment. In the external ophthalmic preparation, the mass percentage of the luteolin-7-O-glucoside or luteolin-7-O-glucuronide is preferably 0.120%, more preferably 1~15%, most preferably 5%. The oral preparation and external ophthalmic preparation can also include an acceptable auxiliary material and/or additive. In the present disclosure, there is no special restrictions on the preparation method of the oral preparation and external ophthalmic preparation, as long as they are prepared by the conventional method of oral preparations and external ophthalmic preparations well known in the art.

Due to the protective effect of luteolin-7-O-glucoside and luteolin-7-O-glucuronide on human retinal pigment epithelial cell damage caused by blue light, the present disclosure also provides use of luteolin-7-O-glucoside as shown in formula I or luteolin-7-O-glucuronide as shown in formula II in an eye healthcare product or food

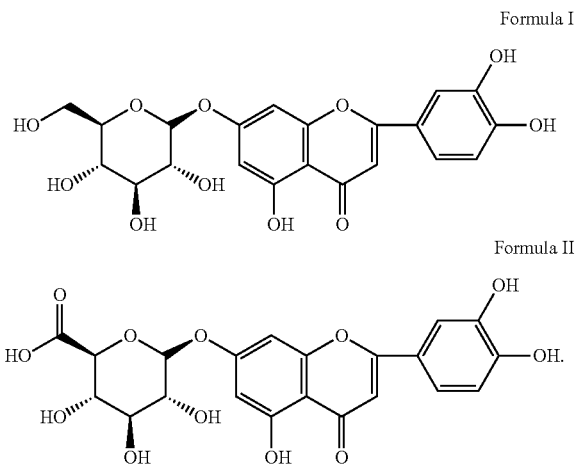

Formula I

Formula II

In the present disclosure, in the eye health care product or food, the mass percentage of luteolin-7-O-glucoside or luteolin-7-O-glucuronide is preferably 0.1%~20%. The present disclosure has no special restrictions on the preparation method of the health product and food, as long as they are prepared by the preparation method of health products and foods well known in the art.

The use of luteolin-7-O-glucoside or luteolin-7-O-glucuronide in the manufacture of a medicament for an eye injury provided by the present disclosure is further described in detail below in conjunction with the examples, which, however, should not be considered as limitation to the scope of the present disclosure.

Example 1

Study on the Cytotoxicity of Luteolin-7-O-Glucoside or Luteolin-7-O-Glucuronide on Human Retinal Pigment Epithelial Cells ARPE-19

ARPE-19 cells (purchased from Guangzhou Jinnuo Biotechnology Co., Ltd., China) were seeded into RPMI-1640 low-glucose cell culture medium containing 10% fetal bovine serum and 1% dual-antibiotics (penicillin-streptomycin) (culture medium containing 2 g/L D-glucose, 0.3 g/L L-glutamine and 2 g/L sodium bicarbonate), and the medium was replaced once every 3 days for future use.

Cells at exponential growth phase were used, and 100 μl of complete medium was added to each well to reach a concentration of $1\times10^4$ cells/mL. Then the cells were cultured in a humidified atmosphere at 37° C. and 5% $CO_2$ for 24 h. After the cells fully adhered, luteolin-7-O-glucoside and luteolin-7-O-glucuronide with final concentrations of 12.5 μmol/L, 25 μmol/L, 50 μmol/L, and 100 μmol/L were added respectively, and cultured for 24 h.

The cell viability was determined by the 3-(4,5-dimethyl-2-thiazolyl)-2,5-diphenyl-2-H-tetrazolium ammonium bromide (MTT) method: 20 μl of 5 mg/ml MTT was added to each well, and the cells were cultured in a $CO_2$ incubator for 4 h, with all operations shielded from light. Then the solvent in the 96-well plate was carefully replaced with 150 μl dimethyl sulfoxide (DMSO), and the plate was shaken for dissolution and crystallization. The absorbance of ARPE-19 cells was measured with a microplate reader at 490 nm, and the cell survival rate was calculated as follows: cell survival rate=(OD value of experimental group−OD value of blank group)/(OD of control group−OD of blank group)×100%.

The results are shown in FIG. 1. The survival rate of cells with adding luteolin-7-O-glucoside (FIG. 1-A) or luteolin-7-O-glucuronide (FIG. 1-B) at the concentration range of 12.5~100 μmol/L were 95.6±5.1%~99.5±5.8%, 94.2±4.7%~96.5±5.4%, respectively. The results show that at the above test concentrations, luteolin-7-O-glucoside and luteolin-7-O-glucuronide had no cytotoxicity on human retinal pigment epithelial cells ARPE-19, indicating that the two compounds have good safety.

Example 2

Study on the Pharmacodynamics of Luteolin-7-O-Glucoside and Luteolin-7-O-Glucuronide on Blue Light-Induced Damage to Human Retinal Pigment Epithelial Cells ARPE-19

ARPE-19 cells were seeded into RPMI-1640 low-glucose cell culture medium containing 10% fetal bovine serum and 1% dual-antibiotics (penicillin-streptomycin), and the medium was replaced once every 3 days for future use.

Cells at exponential growth phase were used, and cells at 500 μl/well were seeded to a 24-well cell culture plate at a concentration of $5\times10^4$ cells/mL, and cultured in a humidified atmosphere at 37° C. and 5% $CO_2$. After the cells fully adhered, the medium was replaced with the DMEM culture medium containing 25 μmol/L N-retinylidene-N-retinyl ethanolamine (A2E) for 2 hours of culture. Then, the supernatant was discarded, and the cells were washed 3 times with PBS, added with the luteolin-7-O-glucoside and luteolin-7-O-glucuronide with final concentrations of 12.5 μmol/L, 25 μmol/L, and 50 pinol/L respectively for 6 h of continuous culture, and then placed in a blue light device (50W LED blue light board with a blue light intensity of 3230~3540 Lux) for 4 h of irradiation. After the light irradiation, the cells were placed in a 37° C. and 5% $CO_2$ incubator again and continued to incubate for 24 h. After incubation, 100 μL of MTT solution with a final concentration of 0.5 mg/mL was added to each well, and incubated for 4 hours shielded from light. Then the supernatant was discarded, and 500 μL of DMSO was added to each well to completely dissolve the formazan. The OD values were measured with a multi-well microplate reader at 490 nm, and the cell survival rate was calculated as follows: cell survival rate=(OD value of experimental group−OD value of blank group)/(OD of control group−OD of blank group)×100%.

It is well-known that A2E, mainly absorbing light of 430 nm wavelength, is phototoxic, which can generate oxygen free radicals to damage cell membranes and intracellular lysosome membranes, and increase the sensitivity to blue light damage. A2E is a classic modeling drug for blue light damage experiments, and A2E was used to build the blue light damage model.

The result is shown in FIG. 2. The cell survival rate of cells in luteolin-7-O-glucoside (FIG. 2-A) and luteolin-7-O-glucuronide (FIG. 2-B) drug intervention groups at the concentration range of 12.5~50 μmol/L were 64.8±6.4%~89.6±2.9% and 62.4±8.3%~84.5±5.2%, respectively, and they were concentration-dependent. Compared with the model group in which ARPE-19 cells were pretreated with A2E and irradiated with blue light (49.5±10.3%), there were significant differences in the luteolin-7-O-glucoside and luteolin-7-O-glucuronide treatment group with different concentrations. (P<0.01, P<0.001). The results show that luteolin-7-O-glucoside and luteolin-7-O-glucuronide have the pharmacodynamic effects of preventing and improving blue light-induced damage to ARPE-19 cells.

Example 3

Study on the Pharmacodynamic Mechanism of Luteolin-7-O-Glucoside on Blue Light-Induced Damage to Human Retinal Pigment Epithelial Cells ARPE-19

A single layer of ARPE-19 cells were seeded and cultured in a 24-well plate with a cell concentration of $5 \times 10^4$ cells/well. After treatment as described in Example 2, the cells were washed twice with PBS and reactive oxygen species (ROS) fluorescent probe dihydroethidium (DHE) staining solution with a concentration of 20 μmol/L was added, and the cells were incubated at 37° C. for 20 min. Then, the cells were washed twice with PBS to fully remove the DHE probe that had not entered the cell, and then imaging was performed under an inverted microscope with an excitation wavelength of 540 nm and an emission wavelength of 590 nm.

The cells were seeded in a 24-well plate ($5 \times 10^4$ cells/well), and after the treatment as previously described, the fix solution was added and incubated for 30 min. Then the cells were washed three times with PBS, added with live cell staining solution (Hoechst 33342) with a concentration of 20 μg/mL, and incubated for 15 min at room temperature shielded from light. After the cells were washed with PBS, imaging was performed under an inverted fluorescence microscope with an excitation wavelength of 365 nm and an emission wavelength of 460 nm.

ROS is one of the important indicators for evaluating cell oxidative stress. As shown in FIG. 3-A, in this experiment, DHE staining was used to detect the intracellular ROS content. It can be seen that after the ARPE-19 cells pretreated with A2E were irradiated with blue light (model group), the fluorescence intensity increased, and the intracellular ROS content increased significantly; while after the intervention of luteolin-7-O-glucoside, the intracellular fluorescence intensity decreased significantly as the dose increased, indicating that luteolin-7-O-glucoside can reduce the accumulation of intracellular ROS by blue light-induced damage. As shown in FIG. 3-B, after the ARPE-19 cells pretreated with A2E were irradiated with blue light, the nucleus underwent obvious condensation and shrinkage, and the fluorescence intensity increased; while after the intervention of luteolin-7-O-glucoside, the cell status had obviously improved, indicating that luteolin-7-O-glucoside can improve blue light-induced cell apoptosis. One of the pharmacodynamic mechanisms of luteolin-7-O-glucoside to prevent and improve blue light-induced damage to human retinal pigment epithelial cells ARPE-19 is to reduce the level of reactive oxygen species and apoptosis of cells, thereby ameliorating the damage to human retinal pigment epithelial cells caused by blue light, and improving impaired vision.

In summary, both luteolin-7-O-glucoside and luteolin-7-O-glucuronide have the effect of preventing and improving blue light-induced damage to human retinal pigment epithelial cells, and can be used for treatment, prevention and improvement of the eye injury caused by blue light.

The above description of the examples is only used to facilitate understanding of the method and core concept of the present disclosure. It should be noted that, for those of ordinary skill in the art, several improvements and modifications can also be made without departing from the principle of the present disclosure, which also fall within the protection scope of the claims thereof. Various modifications to the embodiments are apparent for the skilled in the art. The general principle defined herein may be implemented in other embodiments without departing from the spirit or scope of the present disclosure. Therefore, the present disclosure should not be limited to the embodiments disclosed herein, but has the widest scope in accordance to the principle and the novel features disclosed herein.

The invention claimed is:

1. A method of treating an eye injury, comprising administering luteolin-7-O-glucoside as shown in formula I to a subject in need thereof,

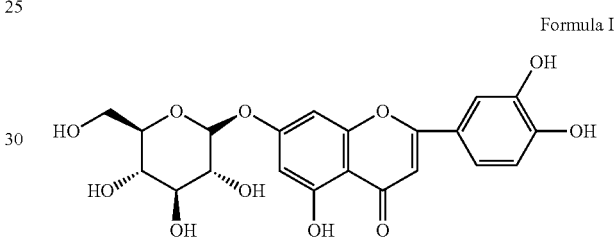

Formula I wherein the eye injury is a human retinal injury caused by blue light.

2. The method according to claim 1, wherein the human retinal injury is human retinal pigment epithelial cell injury.

3. The method according to claim 1, wherein the blue light is short-wave blue light, and the wavelength of the short-wave blue light is 400~500 nm.

4. The method according to claim 3, wherein the blue light is emitted by a mobile phone, a tablet, a television, or a computer monitor.

5. The method according to claim 1, wherein the luteolin-7-O-glucoside is contained in a medicament being an oral preparation or an external ophthalmic preparation;
the oral preparation is tablet, capsule, granule, pill, ointment or oral solution; and
the external ophthalmic preparation is eye drop, ophthalmic gel or ophthalmic ointment.

6. The method according to claim 5, wherein in the oral preparation, the mass percentage of the luteolin-7-O-glucoside is 5%~50%;
in the external ophthalmic preparation, the mass percentage of the luteolin-7-O-glucoside is 0.1%~20%.

* * * * *